United States Patent [19]

Speigel

[11] Patent Number: 5,425,699
[45] Date of Patent: Jun. 20, 1995

[54] METHOD OF MODIFYING HUMAN BEHAVIOR USING SIGNAL TRIGGERED POST-HYPNOTIC SUGGESTION

[76] Inventor: Robert B. Speigel, 6950 93rd Ave. SE., Mercer Island, Wash. 98040

[21] Appl. No.: 867,491

[22] Filed: Apr. 13, 1992

[51] Int. Cl.[6] ........................................ A61M 21/00
[52] U.S. Cl. ............................... 600/26; 128/898
[58] Field of Search ............................ 600/26–28; 128/897–899

[56] References Cited

U.S. PATENT DOCUMENTS 3,908,634 9/1975 Monaghan ........................ 600/28
5,151,080 9/1992 Bick .................................. 600/28

Primary Examiner—Kyle L. Howell
Assistant Examiner—John P. Lacyk
Attorney, Agent, or Firm—Robert H. Sproule

[57] ABSTRACT

A method of modifying human behavior using automatically generated active signals to elicit post-hypnotic suggestions. When a patient is in a hypnotic state, a post-hypnotic suggestion is linked to the active signal. After the hypnotic state has been terminated, the active signal is automatically generated by an appropriate active device in the patient's environ. In this manner, the suggested behavior is reliably elicited without the need for patient intervention.

20 Claims, 2 Drawing Sheets

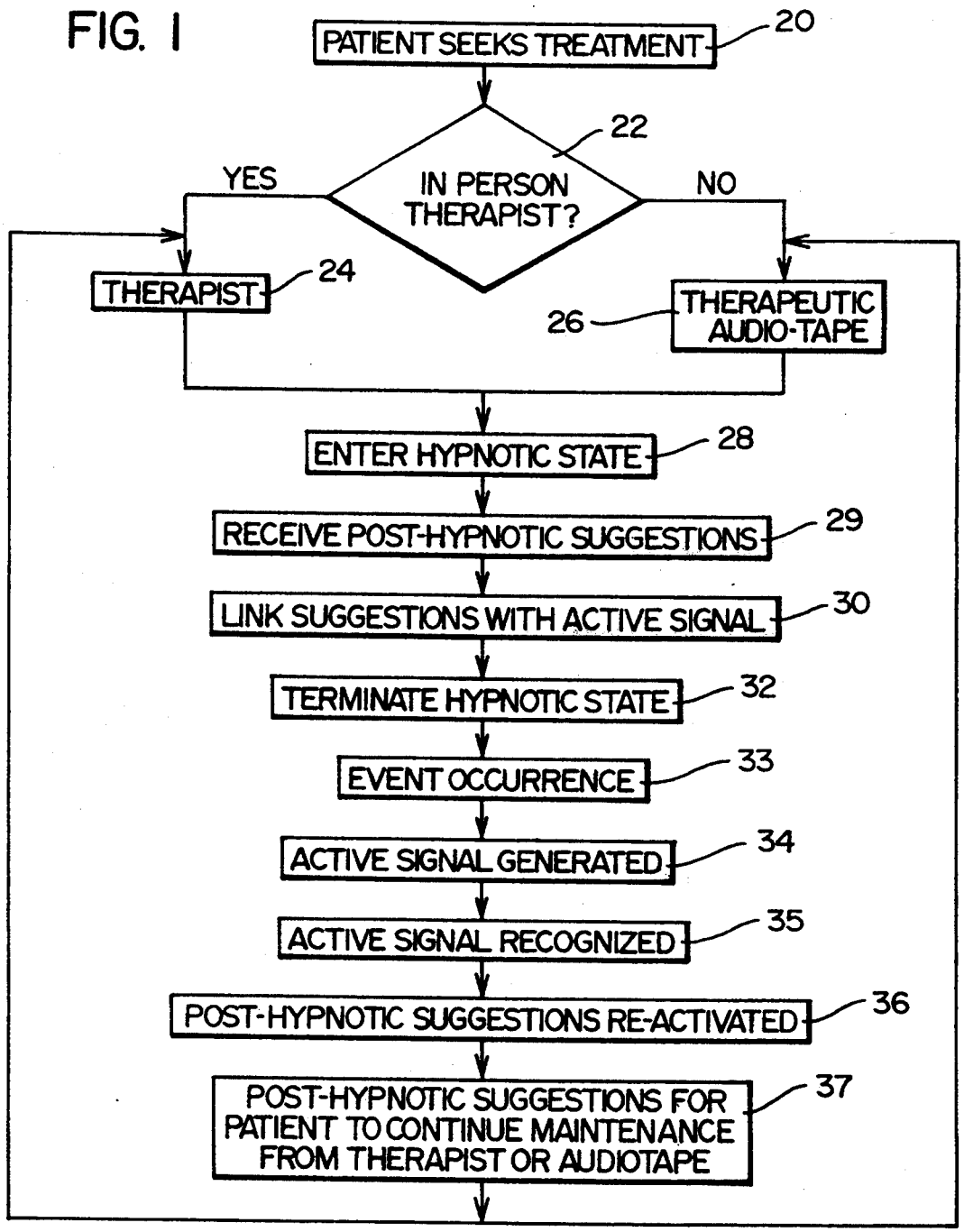

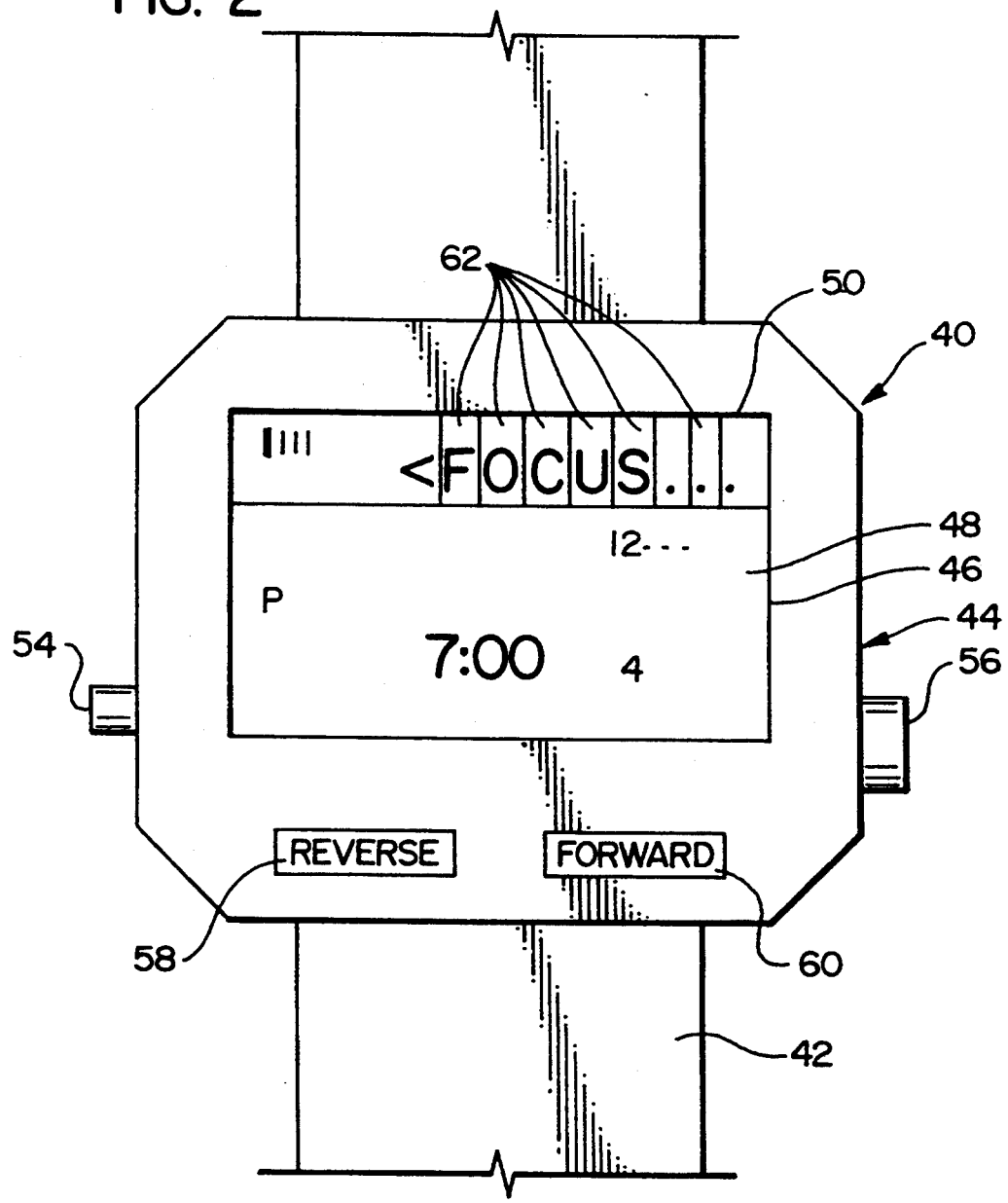

METHOD OF MODIFYING HUMAN BEHAVIOR USING SIGNAL TRIGGERED POST-HYPNOTIC SUGGESTION

TECHNICAL FIELD

The present invention relates to methods of modifying human behavior using a hypnotic process and post-hypnotic suggestions which are elicited by an automatically generated active signal.

BACKGROUND OF THE INVENTION

Clinical hypnotherapy is used to treat a wide variety of psychological problems. The process of clinical hypnotherapy involves helping a patient achieve a very relaxed state and heightened state of suggestibility so that he/she will accept on a subconscious level ideas, beliefs or suggestions he/she might not otherwise be receptive to. The patient's lack of receptivity may be due to stress, tension or certain preconceived ideas. However, the purpose of these suggestions is to disrupt the patient's logic/thought pattern which has created the specific psychological problem.

For example, hypnotherapy may be used to treat people who suffer from extreme test anxiety. Typically, test anxiety results in the patient not fully performing up to his/her capabilities in test taking situations. A typical logic/thought pattern for such a person may be as follows: "If I do badly on the test then I will get a bad grade in the course-then I won't get into college-then I won't become a doctor-then I will be a total failure in life." In the patient's mind, the perceived consequences of performing poorly on the test are tremendous. The resulting anxiety from this logic/thought pattern may actually result in the patient performing substantially below his/her capabilities.

Hypnotherapy involves three separate phases, these being (i) a relaxation phase, (ii) a suggestion phase, and (iii) a post-hypnotic suggestion phase. The process begins with the relaxation phase whereby the therapist helps the patient become more comfortable and relaxed in order for the patient to be receptive to the therapist's suggestions. Once the patient has reached a sufficient level of relaxation, the therapist provides suggestions which are specifically intended to reduce the patient's symptoms. It is the purpose of the hypnotherapy to integrate these suggestions into the patient's subconscious mind so that the suggestions become urges to take a specified action or actions. The therapist will then include one or more suggestions intended to occur after the patient is removed from his/her state of deep relaxation or hypnosis. This set of suggestions are known as "post-hypnotic" suggestions. While they are provided to the patient in the hypnotic state, they are intended to be "cued" by stimuli which will occur later when the patient is no longer in the hypnotic state. That is, the patient is instructed (while in the hypnotic state) to experience the full strength of the post-hypnotic suggestion each time he/she later experiences a specific cue, such as a feeling of anxiety in anticipation of an upcoming test.

For example, the therapist might suggest to the patient (while the patient is in the hypnotic state) that any time he/she experiences anxiety about an upcoming test, to remember and experience the same feelings of relaxation as he/she is feeling while under hypnosis. In this case the post-hypnotic suggestion is "relaxation" which is to be triggered by an internal feeling (cue) of anxiety about an upcoming test (stimulus). Thus, the post-hypnotic suggestions recall the feelings of deep relaxation experienced during hypnosis and the patient "re-experiences" these relaxed feelings thereby disrupting his/her anxiety about the upcoming test situation.

Typically, hypnotherapy sessions are conducted by an experienced therapist who is actually present with the patient. In a formal hypnotherapy session for alleviating such problems as smoking, the therapist will develop a post-hypnotic suggestion which may be unique for the patient. For example, the post-hypnotic suggestion might be that when the patient pulls a cigarette from a cigarette pack, the cigarette will begin to get hotter and hotter between his fingers until he is forced to drop it to keep from being burned. Other suggestions might work better for other patients. For example, the therapist might suggest that the cigarette turns into a wiggling, slimy worm when it is pulled from the cigarette pack. The pack itself could be targeted for a post-hypnotic suggestion. For example it might be suggested that when purchasing cigarettes (the cue), the patient will begin to feel nauseous and dizzy (the post-hypnotic suggestion) and should go out into the street for fresh air.

Suggestions such as these are also used as aids in treatments other than hypnotherapy through the use of vivid images to achieve a desired outcome. For example, non-hypnotic imaging is used in conjunction with radiation and chemotherapy by oncology personnel. The patient usually is told to imagine himself (or a powerful surrogate) "sailing" through the bloodstream, finding and battling the cancer, and finally overcoming it. A patient might imagine herself finding the cancer as a huge knot of gnarled roots blocking her way. She would image that she obtained a small axe and laboriously severed each root, working persistently until the cancer could take no more nourishment from her. As she would cut the roots, they would wither, and finally, the cancer itself would die when all its roots were destroyed.

The current use of formal post-hypnotic suggestion or non-hypnotic heightened suggestibility (including imaging) has been used by mental health or medical professionals who directly (or indirectly through the use of audio-tapes) aid the patient by creating the state of heightened suggestibility and then place the post-hypnotic suggestion. Although suggestion and imaging might be used even in non-therapeutic environments such as sales motivation sessions, the state of heightened suggestibility and the suggestion placement are often controlled by a human session leader or might be delivered through a pre-recorded audio-cassette program.

In the foregoing conventional methods of placing and maintaining post-hypnotic suggestions, the therapist helps create the relaxed state of heightened awareness, places the post-hypnotic suggestion, and then terminates the hypnosis. Afterward, a (hopefully) recognized cue elicits the post-hypnotic suggestion from the patient's subconscious and the suggested behavior results, e.g. relaxation.

A significant problem with these conventional hypnotherapy processes is that post-hypnotic suggestions work well with some types of cues but not with others. Typically, the term "cue" means anything which is intended to elicit a post-hypnotic suggestion. For example, in the case of the post-hypnotic suggestion that a cigarette will start to get hotter and hotter when it is pulled from the cigarette pack and start to burn the smoker's fingers unless it is dropped, the cue might be when the patient reaches for his pack and feels a cigarette placed between his fingers. However, this type of cue is defined herein as an "external passive cue". That is, this cue, although located in the patient's external environment, relies upon the patient's ability to make the suggested connection between an the action of taking a cigarette from an ordinary pack of cigarettes and the heating up of the cigarette so that it burns the patient's fingers. There is nothing different or unusual about the pack of cigarettes to aid the smoker's subconscious mind in making the connection between the cigarette pack and the burning fingers. Furthermore, this particular cue is "object specific". That is, it depends upon the patient obtaining his/her next cigarette from a pack of cigarettes. For example, during a weak moment the patient could consciously bypass this cue (to avoid the unwanted consequences of "burning" fingers) by having his/her spouse or friend pull the cigarette from the pack and place it between his lips.

Another problem with the foregoing conventional hypnotherapy processes is that many of them depend upon the patient awareness of his/her "internal cues". For example, a post-hypnotic suggestion to relax when a patient is feeling anxious about an upcoming test requires the patient to cue on a particular internal state. However, the patient may not be able to recognize his/her internal state at the time. That is, internal cues are not as vivid or well defined as even external passive cues, and may be particularly inaccessible to patients that exhibit certain types of behavioral disorders. In fact, many individuals are normally insensitive to a whole host of internal states such as their internal level of anxiety.

Furthermore, these conventional hypnotherapy processes put the entire responsibility for maintaining the forward progress of the treatment with the patient, who is often the weakest link. This is a particular problem when the patient experiences anxiety or is distracted during the unwanted behavior. It is known that when the patient is in a state of anxiety, he/she is even less likely to initiate the proper steps to trigger the post-hypnotic suggestion.

Also, in terms of overall treatment effectiveness, the patient must remember to re-initiate the original hypnotherapy process each time he/she wants reinforcement of the suggestion. Thus, it is easy for a patient to drift away from the treatment regimen, especially with particularly intractable disorders such as cigarette smoking, alcohol abuse and overeating. It is also known that the post-hypnotic suggestion will degrade over time. That is, the overall strength of the post-hypnotic suggestion's ability to reduce the targeted symptoms will diminish in proportion to the length of time between the placement of the post-hypnotic suggestion and the occurrence of the cue.

SUMMARY OF THE INVENTION

The present invention pertains to a method of treating a behavioral problem of a human subject. The method includes the steps of placing the subject in a psychological state of relaxation and providing a set of post-hypnotic suggestions to the subject, when the subject is in the relaxation state, for overcoming the behavioral problem. In addition, the method includes the steps of informing the subject, when the subject is in the relaxation state, of an active signal which will be generated when the subject is not in the relaxation state, and furthermore that the post-hypnotic suggestions will be triggered in the subject when the subject is exposed to the active signal. Also, the method includes the step of generating the active signal when the subject is not in the relaxation state in response to a predetermined event.

It is therefore an object of the present invention to provide a method for treating human behavioral problems.

It is another object to provide a method of providing post-hypnotic suggestions to a human subject.

It is still another object to provide a method of giving post-hypnotic suggestions which are elicited from a subject in response to an active signal.

It is yet another object to provide a method of automatically generating a trigger signal for eliciting post-hypnotic suggestive behavior.

BRIEF DESCRIPTION OF THE DRAWINGS

These and other objects and advantages of the present invention will be described in further detail in the following Detailed Description in conjunction with the attached drawings, in which:

FIG. 1 is a flow chart describing an overview of the present invention; and

FIG. 2 is plan view of an exemplary active signal device which is used in an exemplary embodiment of the present invention.

DETAILED DESCRIPTION

The present invention is a method for modifying human behavior using post-hypnotic suggestions which are actively triggered in response to a predetermined event. More specifically, the present method involves (i) providing information and instructions, such as by pre-recorded audio-tape, to the patient to achieve a relaxed state of increased suggestibility, (ii) providing a therapeutic post-hypnotic suggestion to the patient which is linked to an active signal which is automatically generated later when the patient is not in the relaxed state, and (iii) then later generating the signal automatically in response to pre-defined threshold events so that the post-hypnotic suggestion is actively triggered in the patient's mind.

In order to further explain the present invention, there will be described hereinafter a specific exemplary embodiment. It should be appreciated that the present invention is not limited to this exemplary embodiment and includes other applications and uses to be explained later in this detailed description.

Referring first to FIG. 1, the present hypnosis embodiment begins with the patient initiating action (block 20) to decide (at decision block 22) whether to use an in-person therapist (block 24) or a hypnotherapy session recorded on audio tape (block 26) sometimes in conjunction with a health professional who is not a professional hypnotherapist. In an exemplary embodiment, the instructions from the therapist are placed on an audio tape (hereinafter referred to as a "therapeutic audio tape"), so that the treatment can be repeated daily by the patient without the actual presence of the therapist. In either case the therapeutic session begins (at block 28) with the therapist helping the patient become more comfortable before entering the hypnotic state. The therapist creates a feeling of empathy and identification with the patient by sharing his/her personal experiences with the patient's symptoms, whether direct or indirect. The therapist shares some personal disclosures or stories designed to help the patient become more familiar with the therapist as a real human being rather than a detached treatment agent.

For example, the therapist may be treating academic performance anxiety in college students. The therapist begins by recalling when he/she was in college and experienced recurring nightmares of an upcoming major test where the therapist (student) entirely "forgot" to open the course book until the night before the test. This nightmare was so unnerving that it resulted in the therapist/student awakening from this nightmare in a state of increased anxiety.

The therapist may then continue with a discussion of the consequences of the patient's symptoms. In the example of academic test anxiety, the consequences/symptoms may include sleep problems, loss of appetite, fatigue, irrational fears, and relationship problems. The therapist may point out that academic performance is seriously impaired by stress. The conclusion, pointed out by the therapist, is that by successfully managing the stressor (performance anxiety), the patient can improve his/her grades.

The therapist then applies academic performance anxiety to the patient's own situation. For example, the therapist informs the patient that typically those people suffering from performance anxiety may not be able to sleep the night before the test. The next morning they might hurriedly eat breakfast, rush to class, begin the exam and read the first question. At this moment, the student may experience "brain lock", and although the student can remember reading the answer during his/her prior studies, he/she just cannot seem to recall it during the test.

The therapist may then begin to help the patient understand the process of hypnosis that he/she is about to undergo. The therapist offers reassurances that the process is quite normal and that the patient will remain in control of the entire event. The therapist engenders the subject's trust that he is competent and expert at the procedure he is about to offer the patient.

During this part of the procedure, the therapist is already beginning to offer hypnotic suggestions that the patient is starting to relax and feel at ease. The therapist is beginning to offer voice and tone inflections that assist the patient in beginning to relax. He is adding comfort and security suggestions to increase the patient's trust and acceptance.

For example, the therapist might provide the following instructions: "Find a quiet place and a comfortable position such as an overstuffed chair. Make sure that it is comfortable for you. Make sure no one will disturb you so that you can have fifteen to twenty minutes of undisturbed quiet. This time is just for you. You deserve it. You have earned it. Sit down and settle into your spot. Allow your body to settle into your seat. Allow yourself to listen only to the sound of my voice. All other sounds blend away. You will feel my instructions happening to you. Take in a deep breath and slowly let it out. Let the air out slowly and completely. Now pull in one more breath of air and breathe through the constrictions you may be feeling. Feel the deep sense of relaxation."

The therapist then enters into a formal hypnosis procedure. This procedure may consist of a numeric countdown from the number ten to the number one, or it may involve a visual image of downward movement such as the patient taking an imaginary elevator ride from the tenth floor to the first floor of a building. The therapist now uses voice inflections and tone consistent with creating a hypnotic state in the patient. The therapist may ask the patient to provide some sort of feedback when he/she is fully relaxed.

For example, the therapist might provide the following instructions: "Now conjure yourself on an elevator. In your mind's eye you are in the elevator. You see the elevator floor, smell the elevator, and see the floor indicator on the elevator wall. The elevator has picked you up on the tenth floor. You feel your body making a slow, safe descent. You feel your body becoming more relaxed. The downward movement of the elevator appears to quicken and you notice your body doubling in relaxation with each passing floor. You have a profound and intense feeling of calm. You are now approaching the first floor. The elevator doors open and you see a scene of peace and solitude. You feel yourself leaving the elevator and moving into this place of calm and solitude. You find a place to rest."

The therapist then enters into the suggestion phase (block 29) of the hypnotherapy. These suggestions consist of visual images and auditory information which are consistent with alleviation of the patient's symptoms. They hold the curative value for the patient's condition and empower the patient to mobilize his/her own processes to overcome the symptoms of his/her condition. These suggestions are repeated several times and in several different ways to assist the subject to integrate the suggestions into his/her subconscious mind.

For example, the therapist might provide the following instructions: "These words are going to a place deep inside you and they will be available whenever you wish to retrieve them. You are a bright and knowledgeable individual. You have achieved much in your life and you can achieve even more. By remaining relaxed and calm you can learn quickly and easily. Information can flow into your brain and can be recovered with similar ease. You can remain calm and relaxed as you proceed through your academic assignments. Worries of how you might perform on a test disappear like the steam off of a hot cup of tea. Fears about your success vanish like a mirage on a desert horizon. Your mind becomes curious and focused. You can remember to remain this focused and relaxed in any situation. The information you have previously gathered in your studies will become available to you as if from a high speed computer with the information displayed on a bright computer screen. You are calm, relaxed and focused. You are calm, relaxed and focused. You realize my words have gone deep inside of you and will remain with you daily."

At this point in the therapy, these lengthy and repeated suggestions are paired with a pre-selected active signal (block 30 in FIG. 1) which will automatically cause the post-hypnotic suggestion to be "triggered" in the patient's mind. In the present application, the term "active signal" means a signal, generated such as for example, in the form of sound, mechanical, electromechanical, or electromagnetic energy. In an exemplary embodiment, the active signal is generated externally of the patient. In addition, the term "trigger" means to elicit or activate the previously placed post-hypnotic suggestions.

In an exemplary embodiment of the present invention, the active signal is an audio signal followed by a visual display of a word and/or icon. This signal is generated from an active device which is available to the patient at the required times. In a further exemplary embodiment, the active device is an electronic device, such as a programmable wrist watch, which is worn on the patient's wrist.

In the present invention, the active device responds to a predetermined event to generate the active signal. The term "predetermined event" is meant to define an occurrence, such as for example, an internal physiological state or an external clock time or physical event, which is being monitored and is known to occur at some future time.

While still in a hypnotic state, the patient is instructed to allow the full strength of the suggestions he/she is currently experiencing to be renewed each time he/she experiences the active signal from the active device. For example, the therapist might provide the following instructions: "These feelings of calm and relaxation and the words I have said to you will be fully renewed with the use of the active signal wristwatch previously programmed to accompany this training. At various times during the day when you wear the wristwatch you will hear this tone from it." The therapist provides the actual tone of the wristwatch which may be a continuous "beeping" sound. The therapist continues instructing the patient that "each time you hear this sound you can remember to look at the face of your watch to view the word 'FOCUS' visually scrolling across the top portion of it. Read the word as it scrolls across the top of the watch. As you view the word 'FOCUS' across the top of the watch you can remember my words. As you view the word 'FOCUS' you can remember my words and become more calm and relaxed. As you read the word 'FOCUS' you can continue the task you are currently engaged in, however as the word 'FOCUS' appears before your eyes, you will be able to subconsciously recall and reinforce all that I have said to you here. 'FOCUS' reminds you to stay totally in the present. 'FOCUS' stimulates you to perform on tests like a computer retrieving its data. All of those thoughts can be retrieved when you see the word 'FOCUS' scrolling across the face of your wristwatch."

The patient is then brought out of his/her hypnotic state (block 32 of FIG. 1) with a count-up from five to one, and the session is ended. For example, the therapist might say "We are now ready to come back from this very relaxed and serene place you have been. This place will remain here for you whenever you need to return to it. In a moment, I will begin counting backward from five to one. When I reach 'three' you can begin to open your eyes, and when I reach 'one' you will open your eyes fully and you will be completely awake."

It should be appreciated that in the present embodiment the use of a two phase active signal further assists the patient in recalling the post-hypnotic suggestion. More specifically, the first phase of the active signal is an audio alarm (the active signal generated at block 34) which is activated by the physiological monitor or when the selected alarm time is reached (the predetermined event occurrence at block 33). The patient has already been conditioned through normal use of the watch to look at his/her watch upon hearing the alarm. The second phase of the active signal is the visual display of the word "FOCUS" on the face of the watch (block 35). The word "FOCUS" has already been repeated and emphasized during the suggestion portion of the therapy. In the patient's mind, the word "FOCUS" has only one connotation (block 36), this being the feeling of focused relaxation and confidence experienced during the previous hypnotherapy session(s) and the reexperiencing of all the connected post-hypnotic suggestions provided while in the hypnotic state.

As indicated above, in an exemplary embodiment, the active device is a wristwatch which in a further embodiment is a model "Telememo 30" manufactured by Casio Ltd of London, England. The wristwatch 40, identified by the numeral 40 in FIG. 2, includes a wrist strap 42 attached to a watch body indicated at 44. The body 44 includes an alphanumerical screen 46 having a lower portion 48 which displays the time and date, and an upper portion 50 which displays alphanumerical characters entered by the user. In addition, the body includes a function button 54 located at its lower left hand corner, a data entry button 56 located at its lower right hand corner, a left "reverse" button 58 and a right "forward" button 60, which are both located below the screen 46. In order to program the watch for active signal generation, the function button 54 is pressed twice to activate the alarm (beeping) function. Then the forward button 60 or the reverse button 58, as the case may be, is pressed to select the desired alarm time or times. Once this is done, the function button 54 is pressed again to select the desired month for alarm operation. Once this is accomplished, the function button 54 is pressed once to access the upper screen portion 50. In this mode, the data entry button 56 is pressed once to enter data, and the forward and reverse buttons are used to step through the alphabet for each character space 62 located on screen portion 50. In an exemplary embodiment, the word "FOCUS" is selected to be the visual cue. Other active signals may be selected depending upon the type suggestion being elicited by the signal. By programming the alarm to display the word "FOCUS" followed by three dots, the word "FOCUS" is caused to continuously scroll across the top portion of the screen after the watch has displayed the selected alarm time and the audible alarm signal has sounded. Instructions for programming words into the watch for display at the screen top portion 50 are conventional and provided with the watch at time of sale.

Having described an exemplary embodiment of the present invention, attention now will be turned to other aspects of the present invention. As described previously, the present invention, instead of relying upon a passive external cue, or an internal cue, provides a post-hypnotic suggestion that is reliably triggered by an active signal that can unmistakably externalize even the most subtle internal states. The active device is programmed to generate the signal in response to a predetermined event. Thus, effective post-hypnotic behavior can be reliably elicited.

In another exemplary embodiment, when the patient is in the hypnotic state, he/she is provided with a further post-hypnotic suggestion (also triggered by the active signal), instructing the patient to seek therapeutic maintenance by returning again to the hypnotic state (at a prescribed time after terminating the hypnotic state) and receiving the post-hypnotic suggestion(s) by use of the therapeutic audio tape or by returning to the therapist (flowblock 37 in FIG. 1). By re-entering the hypnotic state and listening to the post-hypnotic suggestion on a continuing, e.g., daily, basis, the post-hypnotic suggestion is strongly reinforced inside the patient's subconscious (hereinafter referred to as "patient maintenance"). In the exemplary embodiment whereby patient maintenance is performed by the therapeutic audio tape, the entire process of entering the hypnotic state, delivering the post-hypnotic suggestion, and then generating the active signal to elicit the post-hypnotic suggestion can be accomplished automatically and without the further intervention of an in-person therapist. That is, the process cycle, once initiated, regenerates itself automatically. The therapeutic audio tape delivers (i) a therapeutic post-hypnotic suggestion and (ii) a post-hypnotic suggestion to again listen to the audio tape. The patient complies with the post-hypnotic suggestion to listen to the audio tape and again receives the post-hypnotic suggestion. Sometime later when the hypnotic state has been terminated, there is automatic generation of the active signal which elicits post-hypnotic suggestions (i) and (ii). This is followed by the patient responding to the therapeutic suggestion as well as listening again to the therapeutic audio tape.

The method of the present invention may be applied in a number of programs for effectively treating a wide range of dysfunctional behaviors. It has several advantages, including the fact it uses unmistakable active cues for triggering therapeutic post-hypnotic behavior so that post-hypnotic behavior occurs with a high degree of reliability. In addition there is a high degree of control, reliability, and consistency in the final, delivered therapy.

This method of automatically triggered suggestions is more reliable in bringing about behavior and affective changes because it is self-maintaining and because it relies on an unmistakable active signal to elicit desired post-hypnotic behavior. Unlike conventional methods, it does not rely on the patient's sometimes unreliable ability to recognize a cue in his/her internal or external environment. This active signal is a more reliable elicitor of post-hypnotic behavior because it is different from the typical internal and external cues, and because the patient has not had a chance to become numb or to ignore the active signal as might occur with various other internal and passive cues encountered over his/her lifetime.

In addition to the above mentioned active signals of audible tones and visual displays, other active signals may include, for example, a tactile signal such as a vibrating device attached to the back of a wristwatch, or an audible tone followed by a short spoken phrase or verbal guided imagery. These audio signals could be delivered through small speakers or the headphones of an audio cassette player. Similarly, pre-selected visual images can be provided by a small television or computer monitor.

Other types of devices for initiating the generation of an active signal to trigger post-hypnotic suggestions may include pulse rate monitors which continuously monitor the pulse rate of the patient and initiate the generation of an active signal when a preset pulse rate is exceeded. In addition, other such devices may be responsive to predetermined levels of the patient's galvanic skin resistance, blood pressure, brain waves or behavior. With regard to behavioral cues, the active signal device could be activated by a physical action such as the opening of a refrigerator or pantry door by the patient to deliver a post-hypnotic suggestion to overcome a problem of overeating.

What is claimed is:

1. A method of treating behavioral problems of a subject, the method comprising the steps of:
    a. placing the subject in a psychological state of relaxation;
    b. providing a suggestion to the subject, when the subject is in the relaxation state, for overcoming the behavioral problem;
    c. informing the subject, when the subject is in the relaxation state, of an active signal which will be generated when the subject is not in the relaxation state;
    d. informing the subject, when the subject is in the relaxation state, that the suggestion will be recalled by the subject when the subject receives the active signal; and
    e. generating the active signal when the subject is not in the relaxation state in response to a predetermined event in a manner that the subject receives the active signal.

2. The method as set forth in claim 1 wherein the active signal is generated electronically.

3. The method as set forth in claim 1 wherein the active signal is electromagnetic energy.

4. The method as set forth in claim 1 additionally comprising a step of suggesting to the subject, when the subject is in the state of relaxation, to seek repetition of the post-hypnotic suggestion placing step when the subject recognizes the active signal which is generated when the subject is not in the relaxation state.

5. The method as set forth in claim 1 wherein the active signal is generated automatically in response to the predetermined event.

6. The method as set forth in claim 1 wherein the predetermined event is a clock time.

7. The method as set forth in claim 1 wherein the state of relaxation is a hypnotic state.

8. The method as set forth in claim 1 wherein the active signal is an audio signal.

9. The method as set forth in claim 1 wherein the active signal is a visual signal.

10. The method as set forth in claim 9 wherein the visual signal is a predetermined word.

11. The method as set forth in claim 1 wherein the active signal is generated by an electronic device carried by the subject.

12. The method as set forth in claim 1 wherein the active signal is generated by a watch carried by the subject.

13. The method as set forth in claim 1 wherein:
    a. the active signal is an audio output followed by a visual output; and
    b. the active signal is generated by a watch carried by the subject.

14. The method as set forth in claim 13 wherein the visual output is a predetermined displayed word.

15. The method as set forth in claim 1 wherein the suggestion is to be relaxed and focused.

16. The method as set forth in claim 13 wherein:
    a. the active signal is generated by a wristwatch worn by the subject;
    b. the visual output is displayed by the wristwatch; and
    c. the suggestion to be recalled by the subject viewing the visual output is a post-hypnotic suggestion.

17. The method as set forth in claim 1 wherein steps a through d are audio instructions provided to the subject by an audio output from an audio tape player.

18. A method of treating behavioral problems of a subject, the method comprising the steps of:
    a. placing the subject in a psychological state of relaxation;

b. providing a suggestion to the subject, when the subject is in the relaxation state, for overcoming the behavioral problem;

c. informing the subject, when the subject is in the relaxation state, of an active signal which will be generated by a wristwatch when the subject is not in the relaxation state;

d. informing the subject, when the subject is in the relaxation state, that the suggestion will be recalled by the subject when the subject recognizes an audio signal generated by the wristwatch and views a visual display on the wristwatch; and e. generating the audio and visual signals when the subject is not in the relaxed state in a manner that the signals are generated electronically in response to an occurrence of a predetermined clock time of the wristwatch.

19. A method of treating behavioral problems of a subject, the method comprising the steps of:

a. placing the subject in a state of psychological relaxation;

b. providing a suggestion to the subject, when the subject is in the relaxation state, for overcoming the behavioral problem;

c. informing the subject, when the subject is in the relaxation state, of an active signal that will be generated when the subject is not in the relaxation state;

d. generating the active signal so that the subject receives the active signal when in the relaxation state;

e. informing the subject, when the subject is in the relaxation state, that the suggestion will be recalled by the subject when the subject is not in the relaxation state and the subject receives the active signal; and f. generating the active signal, when the subject is not in the relaxation state, in response to a predetermined event in a manner that the subject receives the active signal.

20. The method as set forth in claim 19 wherein the active signal generating step when the subject is not in the relaxation state additionally includes the steps of:

a. monitoring a condition to detect the occurrence of the predetermined event; and b. detecting the occurrence of the predetermined event.

* * * * *